US010265057B2

(12) United States Patent
Herzlinger et al.

(10) Patent No.: US 10,265,057 B2
(45) Date of Patent: Apr. 23, 2019

(54) ENDOSCOPE CONTROL SYSTEM

(71) Applicant: INTUITIVE SURGICAL OPERATIONS, INC., Sunnyvale, CA (US)

(72) Inventors: Peter M. Herzlinger, Saratoga, CA (US); Govinda Payyavula, Fremont, CA (US); Brian E. Miller, Los Gatos, CA (US)

(73) Assignee: INTUITIVE SURGICAL OPERATIONS, INC., Sunnyvale, CA (US)

( * ) Notice: Subject to any disclaimer, the term of this patent is extended or adjusted under 35 U.S.C. 154(b) by 276 days.

(21) Appl. No.: 14/909,976

(22) PCT Filed: Aug. 7, 2014

(86) PCT No.: PCT/US2014/050217
§ 371 (c)(1),
(2) Date: Feb. 3, 2016

(87) PCT Pub. No.: WO2015/023513
PCT Pub. Date: Feb. 19, 2015

(65) Prior Publication Data
US 2016/0183930 A1     Jun. 30, 2016

Related U.S. Application Data

(60) Provisional application No. 61/865,996, filed on Aug. 14, 2013.

(51) Int. Cl.
*A61B 17/00*     (2006.01)
*G06F 3/01*      (2006.01)
(Continued)

(52) U.S. Cl.
CPC .......... *A61B 17/00* (2013.01); *A61B 1/00006* (2013.01); *A61B 1/00039* (2013.01);
(Continued)

(58) Field of Classification Search
CPC ................... A61B 17/00; A61B 34/30; A61B 2034/301–2034/303; A61B 34/37;
(Continued)

(56) References Cited

U.S. PATENT DOCUMENTS 5,911,036 A    6/1999  Wright et al.
6,120,433 A *  9/2000  Mizuno .................. A61B 34/70
                                                    600/102

(Continued)

FOREIGN PATENT DOCUMENTS

JP    2000218575 A    8/2000
KR    20110049703 A   5/2011

OTHER PUBLICATIONS

Eterne KR 20110049703 (A)—English Translation Attached, Foreign Reference provided by Applicant.*

(Continued)

*Primary Examiner* — Ryan Henderson
*Assistant Examiner* — Pamela F Wu
(74) *Attorney, Agent, or Firm* — Haynes and Boone, LLP

(57) ABSTRACT

Control of the endoscope in a surgical system is described. In some embodiments, the endoscope can be controlled by movement of the surgeon's head or face at a surgeon's console. In some embodiments, the endoscope can be controlled using sensors integrated with a surgeon's headrest mounted on the surgeon's console.

20 Claims, 17 Drawing Sheets

(51) Int. Cl.
  *A61B 34/30* (2016.01)
  *A61B 34/37* (2016.01)
  *A61B 1/00* (2006.01)
  *A61B 34/00* (2016.01)
  *A61B 90/60* (2016.01)
  *A61B 90/50* (2016.01)
(52) U.S. Cl.
  CPC .............. *A61B 34/30* (2016.02); *A61B 34/37* (2016.02); *G06F 3/012* (2013.01); *G06F 3/013* (2013.01); *A61B 1/00133* (2013.01); *A61B 90/60* (2016.02); *A61B 2017/00199* (2013.01); *A61B 2017/00216* (2013.01); *A61B 2034/301* (2016.02); *A61B 2034/742* (2016.02); *A61B 2090/502* (2016.02); *A61B 2562/0247* (2013.01); *A61B 2562/0257* (2013.01); *A61B 2562/04* (2013.01)
(58) Field of Classification Search
  CPC .......... A61B 1/00004; A61B 1/00006; A61B 1/00039; A61B 2017/00199; A61B 2017/00216; G06F 3/01; G06F 3/011–3/013; G06F 3/016
  USPC ....................................................... 600/118
  See application file for complete search history.

(56) References Cited

U.S. PATENT DOCUMENTS

| | | | |
|---|---|---|---|
| 2009/0248036 A1* | 10/2009 | Hoffman | A61B 1/045 606/130 |
| 2011/0238079 A1 | 9/2011 | Hannaford et al. | |
| 2011/0282140 A1 | 11/2011 | Itkowitz et al. | |
| 2012/0069166 A1 | 3/2012 | Kunz et al. | |
| 2013/0038707 A1* | 2/2013 | Cunningham | H04N 7/183 348/65 |

OTHER PUBLICATIONS

International Search Report and Written Opinion for Application No. PCT/US14/50217, dated Nov. 19, 2014, 12 pages.
Vertut, Jean and Phillipe Coiffet, Robot Technology: Teleoperation and Robotics Evolution and Development, English translation, Prentice-Hall, Inc., Inglewood Cliffs, NJ, USA 1986, vol. 3A, 332 pages.

* cited by examiner

ENDOSCOPE CONTROL SYSTEM

CROSS REFERENCE TO RELATED APPLICATIONS

The present application is a U.S. National Stage patent application of International Patent Application No. PCT/US2014/050217, filed on 7 Aug. 2014 (Aug. 7, 2014), the benefit of which is claimed and the disclosure of which is incorporated herein by reference in its entirety.

TECHNICAL FIELD

Embodiments of the present invention are related to instrument control, and in particular to control of instruments used in minimally invasive robotic surgery.

DISCUSSION OF RELATED ART

Surgical procedures can be performed through a surgical robot in a minimally invasive manner. The benefits of a minimally invasive surgery are well known and include less patient trauma, less blood loss, and faster recovery times when compared to traditional, open incision surgery. In addition, the use of robot surgical systems (e.g., teleoperated robotic systems that provide telepresence), such as the da Vinci™ Surgical System manufacture by Intuitive Surgical, Inc. of Sunnyvale, Calif., is known. Such robotic surgical systems may allow a surgeon to operate with intuitive control and increased precision when compared to manual minimally invasive surgeries.

In a minimally invasive surgical system, surgery is performed by a surgeon controlling the robot. The robot includes one or more instruments that are coupled to robot arms. The instruments access the surgical area through small incisions through the skin of the patient. A cannula is inserted into the incision and a shaft of the instrument can be inserted through the cannula to access the surgical area. An endoscope can be used to view the surgical area. In many cases, the surgeon can control one instrument at a time. If the surgeon wants to change the view of the endoscope, control is shifted from the current surgical instrument to the endoscope, the surgeon manipulates the endoscope, and control is shifted back to the surgical instrument.

Therefore, there is a need to develop better surgical systems for robotic minimum invasive surgeries.

SUMMARY

In accordance with aspects of the present invention, movement of an image of the surgery can be controlled by motion of the surgeon's head or face at the surgeon's console. In some embodiments, for example, a surgeon's console includes an image display system that displays an image of a surgical area; and at least one sensor mounted in the surgeon's console to provide a signal related to a movement of the surgeon's face, the image being moved according to the signal.

In some embodiments, a headrest for a surgical console includes a forehead rest surface; a headrest mount that can attach to the surgical console; and one or more sensors in the headrest that detect inputs from a surgeon's head and provides signals to an endoscope control.

In some embodiments, an endoscope control system includes endoscope controls that receive signals that indicate movement of a surgeon's head and provide an indication of movement of an image received by an endoscope; endoscope manipulation configured to receive the indication of movement of an image and generate signals to affect movement of the endoscope to control the movement of the image; and actuators that can be coupled to the endoscope, the actuators receive the signals to affect movement and control the endoscope to provide the movement.

These and other embodiments are further discussed below with respect to the following figures.

DETAILED DESCRIPTION

Figure 1A:
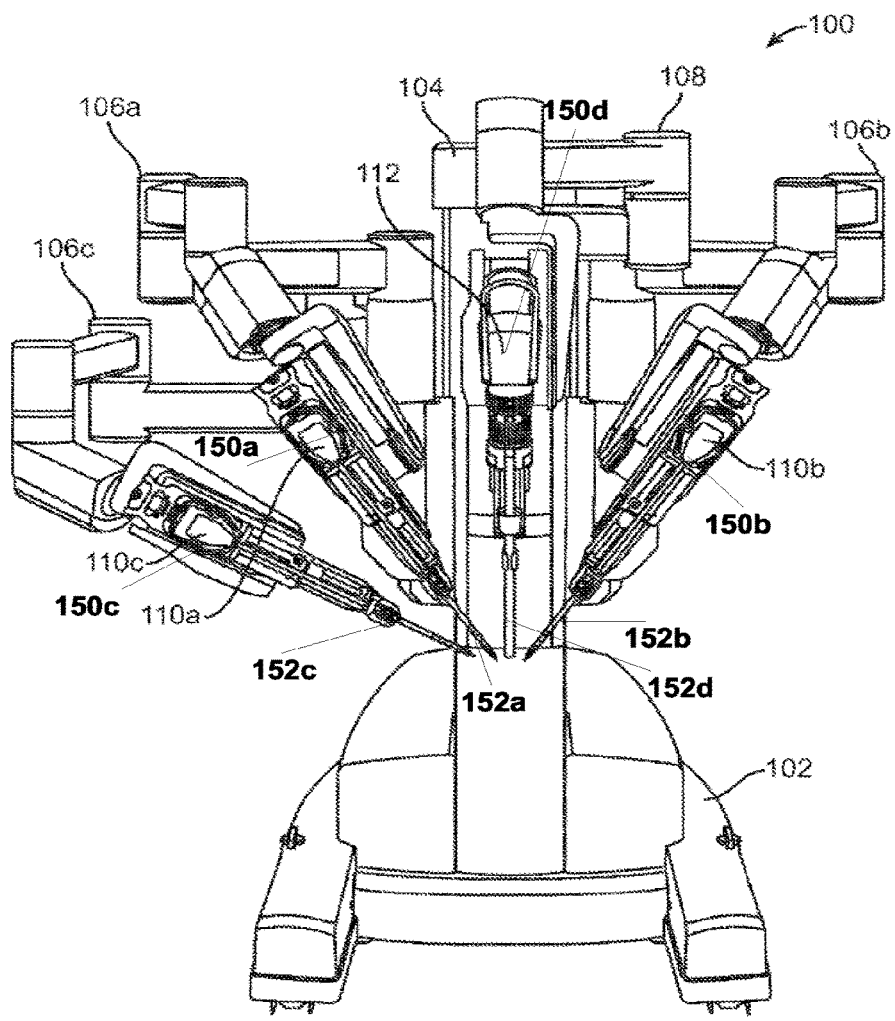
FIGS. 1A, 1B, and 1C illustrate components of an example teleoperated robotic surgical system.

In the following description, specific details are set forth describing some embodiments of the present invention. It will be apparent, however, to one skilled in the art that some embodiments may be practiced without some or all of these specific details. The specific embodiments disclosed herein are meant to be illustrative but not limiting. One skilled in the art may realize other elements that, although not specifically described here, are within the scope and the spirit of this disclosure.

This description and the accompanying drawings that illustrate inventive aspects and embodiments should not be taken as limiting—the claims define the protected invention. Various mechanical, compositional, structural, and operational changes may be made without departing from the spirit and scope of this description and the claims. In some instances, well-known structures and techniques have not been shown or described in detail in order not to obscure the invention.

Additionally, the drawings are not to scale. Relative sizes of components are for illustrative purposes only and do not reflect the actual sizes that may occur in any actual embodiment of the invention. Like numbers in two or more figures represent the same or similar elements.

Further, this description's terminology is not intended to limit the invention. For example, spatially relative terms—such as "beneath", "below", "lower", "above", "upper", "proximal", "distal", and the like—may be used to describe one element's or feature's relationship to another element or feature as illustrated in the figures. These spatially relative terms are intended to encompass different positions (i.e., locations) and orientations (i.e., rotational placements) of a device in use or operation in addition to the position and orientation shown in the figures. For example, if a device in the figures is turned over, elements described as "below" or "beneath" other elements or features would then be "above" or "over" the other elements or features. Thus, the exemplary term "below" can encompass both positions and orientations of above and below. A device may be otherwise oriented (rotated 90 degrees or at other orientations) and the spatially relative descriptors used herein interpreted accordingly. Likewise, descriptions of movement along and around various axes includes various special device positions and orientations. In addition, the singular forms "a", "an", and "the" are intended to include the plural forms as well, unless the context indicates otherwise. And, the terms "comprises", "comprising", "includes", and the like specify the presence of stated features, steps, operations, elements, and/or components but do not preclude the presence or addition of one or more other features, steps, operations, elements, components, and/or groups. Components described as coupled may be electrically or mechanically directly coupled, or they may be indirectly coupled via one or more intermediate components.

Elements and their associated aspects that are described in detail with reference to one embodiment may, whenever practical, be included in other embodiments in which they are not specifically shown or described. For example, if an element is described in detail with reference to one embodiment and is not described with reference to a second embodiment, the element may nevertheless be claimed as included in the second embodiment.

Aspects of embodiments of the invention are described within the context of a particular implementation of a robotic surgical system. Knowledgeable persons will understand, however, that inventive aspects disclosed herein may be embodied and implemented in various ways, including robotic and non-robotic embodiments and implementations. The implementations disclosed here are merely exemplary and are not to be considered as limiting the scope of the inventive aspects disclosed herein.

Figure 1B:
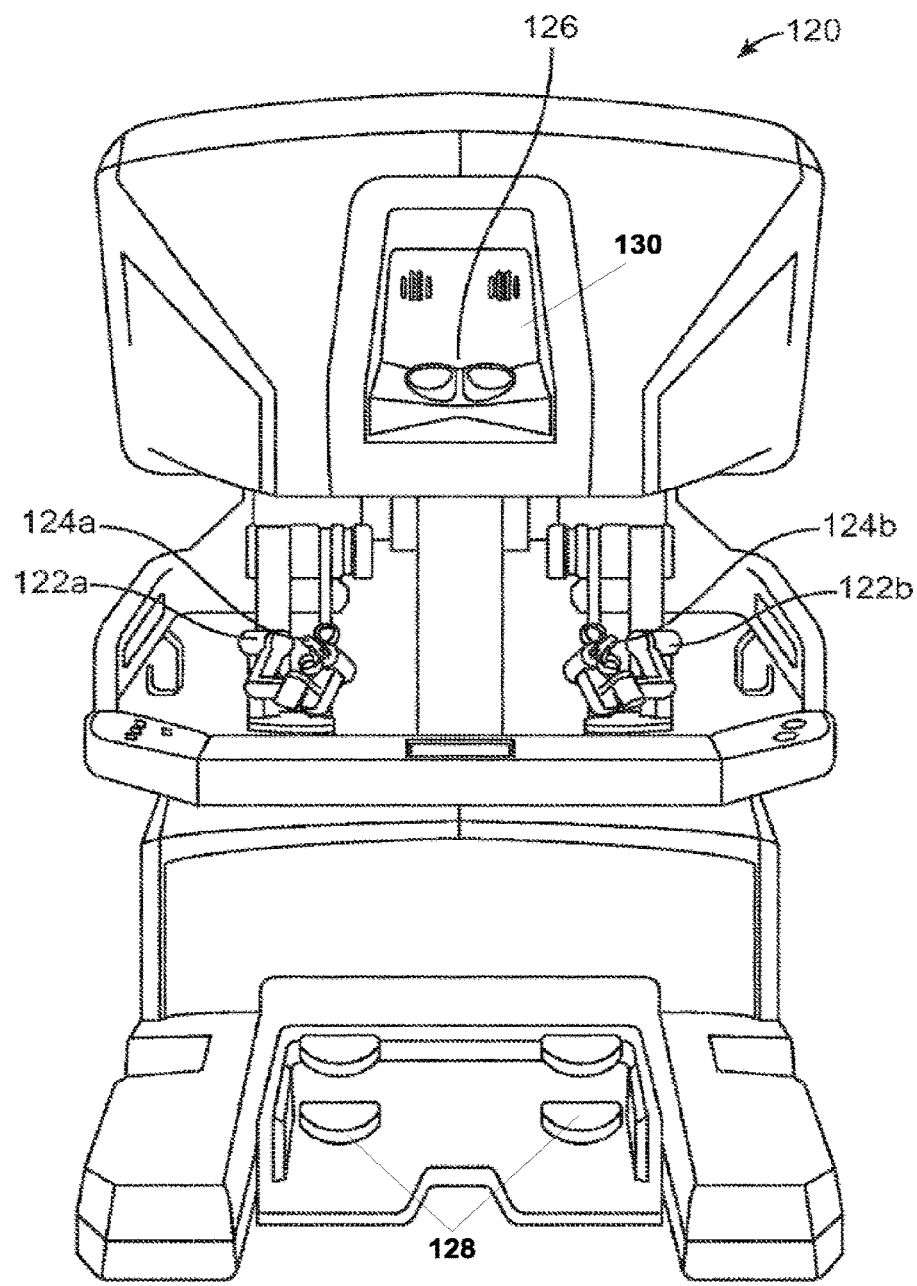
Figure 1C:
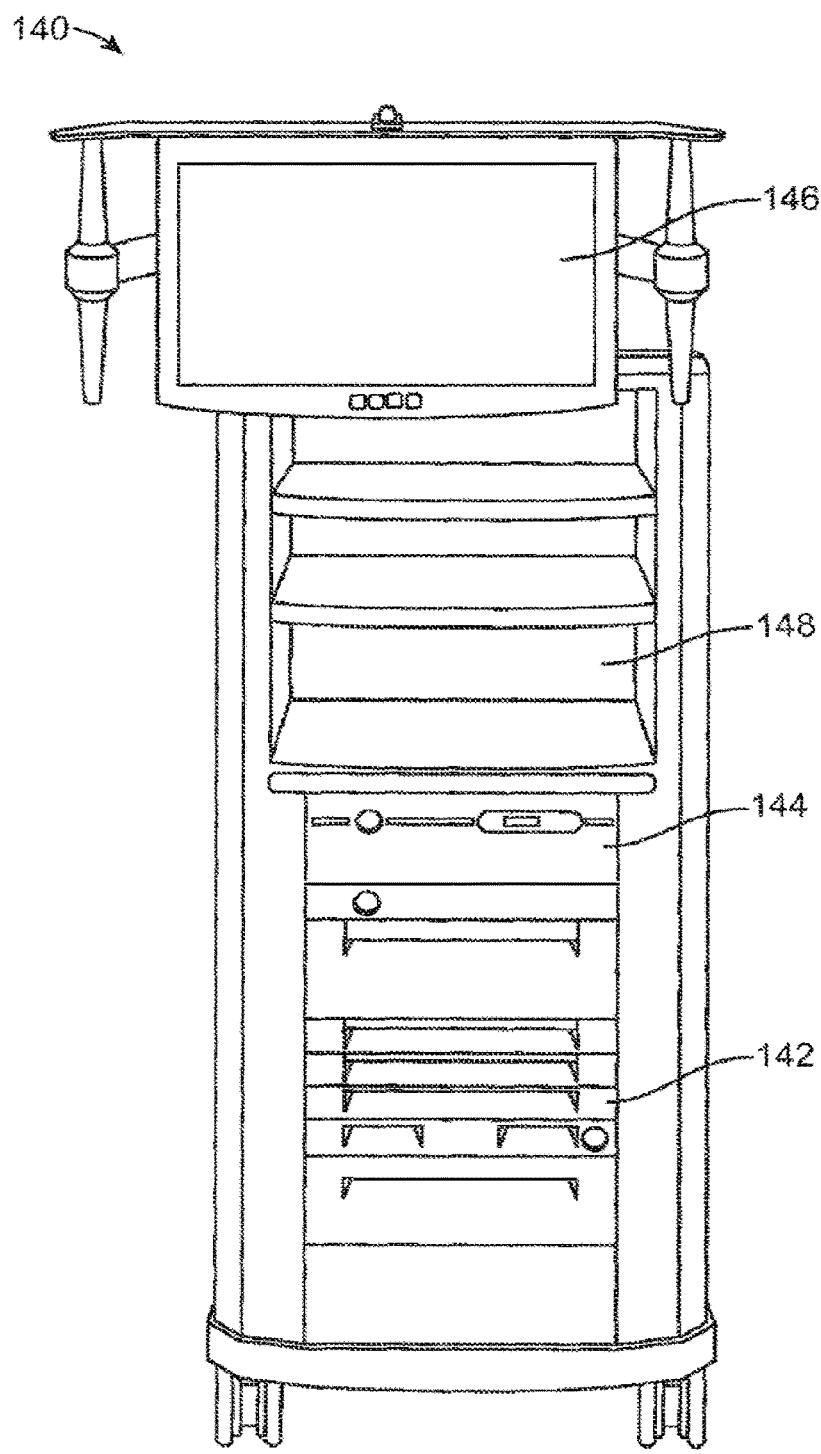

FIGS. 1A, 1B, and 1C are front elevation views of three main components of a teleoperated robotic surgical system for minimally invasive surgery. These three components are interconnected so as to allow a surgeon, with the assistance of a surgical team, to perform diagnostic and corrective surgical procedures on a patient.

FIG. 1A is a front elevation view of the patient side cart component 100 of, for example, the da Vinci™ Surgical System. The patient side cart includes a base 102 that rests on the floor, a support tower 104 that is mounted on the base 102, and several arms that support surgical tools. As shown in FIG. 1A, arms 106a, 106b, and 106c are instrument arms that support and move the surgical instruments used to manipulate tissue. Arm 108, for example, can be a camera arm that supports and moves an endoscope instrument 112. Instrument arm 106c can be an optional third instrument arm that is supported on the back side of support tower 104 and that can be positioned to either the left or right side of the patient side cart as necessary to conduct a surgical procedure. FIG. 1A further shows interchangeable surgical instruments 110a, 110b, 110c mounted on the instrument arms 106a, 106b, 106c, and it shows endoscope 112 mounted on the camera arm 108. Knowledgeable persons will appreciate that the arms that support the instruments and the camera may also be supported by a base platform (fixed or moveable) mounted to a ceiling or wall, or in some instances to another piece of equipment in the operating room (e.g., the operating table). Likewise, they will appreciate that two or more separate bases may be used (e.g., one base supporting each arm).

As is further illustrated in FIG. 1A, instruments 110a, 110b, 110c, and endoscope 112 include an instrument interface 150a, 150b, 150c, and 150d, respectively, and an instrument shaft 152a, 152b, 152c, and 152d, respectively. In some embodiments, component 100 can include supports for cannulas that fix instruments 110a, 110b, 110c, and endoscope 112 with respect to the cannulas.

Further, portions of each of the instrument arms 106a, 106b, 106c, and 108 are adjustable by personnel in the operating room in order to position instruments 110a, 110b, 110c, and endoscope 112 with respect to a patient. Other portions of arms 106a, 106b, 106c, and 108 are actuated and controlled by the surgeon at a surgeon's console 120. Surgical instruments 110a, 110b, 110c, and endoscope 112, can also be controlled by the surgeon at surgeon's console 120.

FIG. 1B is a front elevation view of a surgeon's console 120 component of an example surgical system. The surgeon's console 120 is equipped with left and right multiple degree-of-freedom (DOF) master tool manipulators (MTM's) 122a, 122b, which are kinematic chains that are used to control the surgical tools. The surgeon grasps a pincher assembly 124a, 124b on each MTM 122, typically with the thumb and forefinger, and can move the pincher assembly to various positions and orientations. When a tool control mode is selected, each MTM 122 is coupled to control a corresponding instrument and instrument arm 106 for the patient side cart 100. For example, left MTM 122a may be coupled to control instrument arm 106b and instrument 110a, and right MTM 122b may be coupled to control instrument arm 106b and instrument 110b. If the third instrument arm 106c is used during a surgical procedure and is positioned on the left side, then left MTM 122a can be switched between controlling arm 106a and instrument 110a to controlling arm 106c and instrument 110c. Likewise, if the third instrument arm 106c is used during a surgical procedure and is positioned on the right side, then right MTM 122a can be switched between controlling arm 106b and instrument 110b to controlling arm 106c and instrument 110c. In some instances, control assignments between MTM's 122a, 122b and arm 106a/instrument 110a combination and arm 106b/instrument 110b combination may also be exchanged. This may be done, for example, if the endoscope is rolled 180 degrees, so that the instrument moving in the endoscope's field of view appears to be on the same side as the MTM the surgeon is moving. The pincher assembly is typically used to operate a jawed surgical end effector (e.g., scissors, grasping retractor, needle driver, and the like) at the distal end of an instrument 110.

Additional controls are provided with foot pedals 128. Each of foot pedals 128 can activate certain functionality on the selected one of instruments 110. For example, foot pedals 128 can activate a drill or a cautery tool or may operate irrigation, suction, or other functions. Multiple instruments can be activated by depressing multiple ones of pedals 128. Certain functionality of instruments 110 may be activated by other controls.

Surgeon's console 120 also includes a stereoscopic image display 126. Left side and right side images captured by the stereoscopic endoscope 112 are output on corresponding left and right displays, which the surgeon perceives as a three-dimensional image on display system 126. In an advantageous configuration, the MTMs 122 are positioned below display system 126 so that the images of the surgical tools shown in the display appear to be co-located with the surgeon's hands below the display. This feature allows the surgeon to intuitively control the various surgical tools in the three-dimensional display as if watching the hands directly. Accordingly, the MTM servo control of the associated instrument arm and instrument is based on the endoscopic image reference frame.

The endoscopic image reference frame is also used if the MTM's 122 are switched to a camera control mode. In some cases, if the camera control mode is selected, the surgeon may move the distal end of the endoscope 112 by moving one or both of the MTM's 122 together (portions of the two MTM's 122 may be servomechanically coupled so that the two MTM portions appear to move together as a unit). The surgeon may then intuitively move (e.g., pan, tilt, zoom) the displayed stereoscopic image by moving the MTM's 122 as if holding the image in the hands.

As is further shown in FIG. 1B, a headrest 130 is positioned above display system 126. As the surgeon is looking through display system 126, the surgeon's forehead is positioned against headrest 130. In some embodiments of the present invention, manipulation of endoscope 112 or other instruments can be achieved through manipulation of headrest 130 instead of utilization of MTM's 122. In some embodiments, headrest 130 can, for example, include pressure sensors, a rocker plate, optically monitored slip plate, or other sensors that can detect movement of the surgeon's head. As such, headrest 130 includes a device that monitors and tracks motion of the surgeon's head. In each of these cases, the data indicating the motion of the surgeon's head can be used to manipulate endoscope 112 in order to change the image displayed on display system 126.

The surgeon's console 120 is typically located in the same operating room as the patient side cart 100, although it is positioned so that the surgeon operating the console is outside the sterile field. One or more assistants typically assist the surgeon by working within the sterile surgical field (e.g., to change tools on patient side cart 100, to perform manual retraction, etc.). Accordingly, the surgeon operates remote from the sterile field, and so the console may be located in a separate room or building from the operating room. In some implementations, two consoles 120 (either co-located or remote from one another) may be networked together so that two surgeons can simultaneously view and control tools at the surgical site.

FIG. 1C is a front elevation view of a vision cart component 140 of a surgical system. The vision cart 140 can, for example, house the surgical system's central electronic data processing unit 142 and vision equipment 144. The central electronic data processing unit includes much of the data processing used to operate the surgical system. In various other implementations, however, the electronic data processing may be distributed in the surgeon console 120 and patient side cart 100. The vision equipment includes camera control units for the left and right image capture functions of the stereoscopic endoscope 112. The vision equipment also includes illumination equipment (e.g., Xenon lamp) that provides illumination for imaging the surgical site. As shown in FIG. 1C, the vision cart includes an optional touch screen monitor 146 (for example a 24-inch monitor), which may be mounted elsewhere, such as on the patient side cart 100. The vision cart 140 further includes space 148 for optional auxiliary surgical equipment, such as electrosurgical units, insufflators, suction irrigation instruments, or third-party cautery equipment. The patient side cart 100 and the surgeon's console 120 are coupled, for example via optical fiber communications links, to the vision cart 140 so that the three components together act as a single teleoperated minimally invasive surgical system that provides an intuitive telepresence for the surgeon. And, as mentioned above, a second surgeon's console may be included so that a second surgeon can, e.g., proctor the first surgeon's work.

During a typical surgical procedure with the robotic surgical system described with reference to FIGS. 1A-1C, at least two incisions are made into the patient's body (usually with the use of a trocar to place the associated cannula). One incision is for the endoscope camera instrument, and the other incisions are for the surgical instruments. In some surgical procedures, several instrument and/or camera ports are utilized to provide access and imaging for a surgical site. Although the incisions are relatively small in comparison to larger incisions used for traditional open surgery, a minimum number of incisions is desired to further reduce patient trauma and for improved cosmesis.

Figure 2:
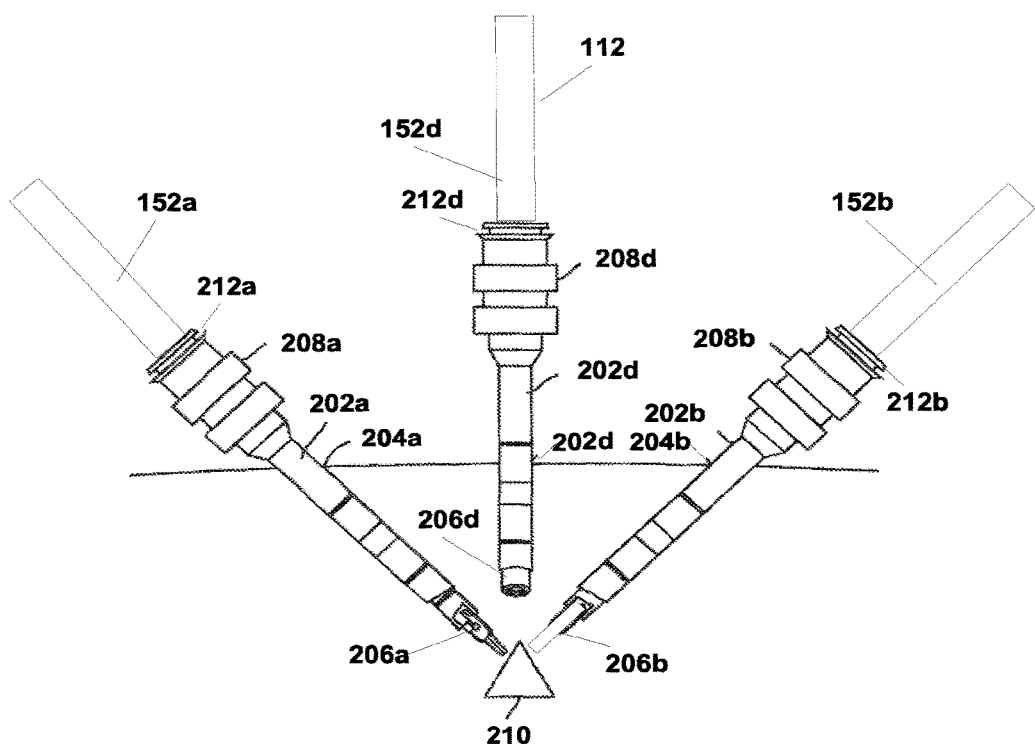
FIG. 2 illustrates cannulas as utilized by the system of FIGS. 1A, 1B, and 1C.

FIG. 2 illustrates utilization of the surgical instruments illustrated in FIGS. 1A, 1B, and 1C. As shown in FIG. 2, shafts 152a, 152b, and 152d pass through cannulas 202a, 202b, and 202d, respectively. Cannulas 202a, 202b, and 202d extend through instrument incisions 204a, 204b, and 204d, respectively. As is shown in FIG. 2, shafts 152a, 152b, and 152d extend through cannulas 202a, 202b, and 202d, respectively. End effectors 206a, 206b, and 206d are attached to shafts 152a, 152b, and 152d, respectively. As discussed above, end effectors 206a, and 206b can be jawed surgical end effectors (e.g., scissors, grasping retractor, needle driver, and the like). Further, end effector 206c is illustrated as an endoscope tip. As shown in FIG. 2, cannulas 202a, 202b, and 202d and shafts 152a, 152b, and 152d are positioned so that end effectors 206a, 206b, and 206d operate in a surgical area 210.

As shown in FIG. 2 cannulas 202a, 202b, and 202d include mounting fittings 208a, 208b, and 208d, respectively, that can be engaged by arms 106a, 106b, and endoscope arm 108, respectively, to allow for very little movement of the instrument end effectors 206a, 206b, and 206d, respectively, as possible. Cannulas 202a, 202b, and 202d further include cannula seal mounts 212a, 212b, and 212d, respectively.

During surgery, particularly if the surgery is abdominal surgery, pressurized $CO_2$ can be utilized to expand the abdomen, allowing for better access to surgical area 210. Cannula seals attached to cannula seal mounts 212a, 212b, and 212d prevent leakage of fluids or other materials from the patient.

During the operation, the surgeon sitting at surgeon's console 120 can manipulate end effectors 206a, 206b, and 206d as well as move shafts 152a, 152b, and 152d along their lengths. In the particular arrangement illustrated in FIG. 2, instrument 206d is illustrated as an endoscope, instrument 206a can be, for example, a cautery tool, and instrument 206b can be, for example, a suction irrigator tool. While the surgeon needs to control instruments 206a and 206d with the MTMs 122, it is difficult to further control the endoscopic camera of instrument 112. Therefore, some embodiments of the present invention provide another control mechanism in order to allow the surgeon to use sensors on a headrest to control endoscopic camera instrument 112 while continuing to manipulate MTMs 122 to control surgical instruments 206a and 206b.

According to some embodiments of the invention, a sensing method allows for the surgeon to manipulate the headrest in order to control, for example, the endoscopic camera while separately using MTMs 122 to control the surgical instruments. Some embodiments of the present invention can eliminate the need to switch modes from instrument control to camera control, and then back again, when it is necessary to reposition the camera. In some embodiments, positioning the camera or control of the camera zoom level can be accomplished while the surgical instruments are actively being controlled by the surgeon.

As shown in FIG. 2, endoscope 112 includes shaft 152d that passes through cannula 202d. End effector 206d at the distal end of shaft 152d can include optics and mechanics to illuminate surgical area 210 and capture an image, in some cases a stereo image, of surgical area 210. Although FIGS. 1A, 1B, 1C and 2 illustrate, for example, a multi-port robotic surgical system, embodiments of the present invention can also be used in a single-port robotic surgical system. In general, embodiments of the present invention can be used with any robotic surgical system where the surgeon is controlling instruments from a remote panel.

Figure 3:
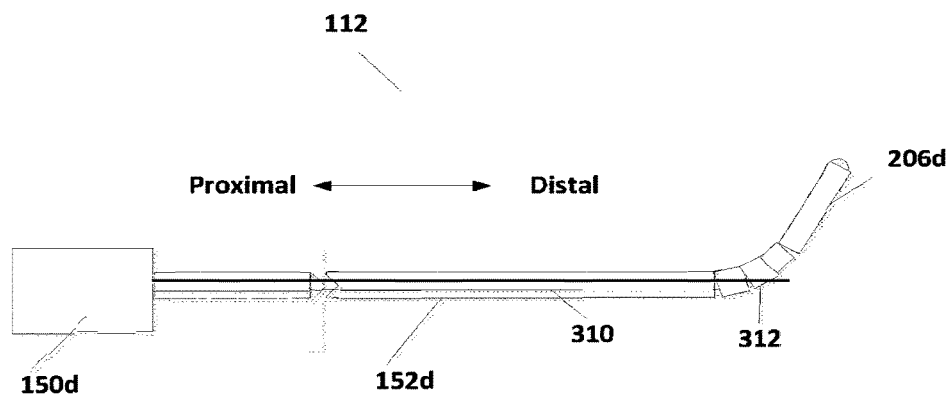
FIG. 3 illustrates an endoscope that can be utilized with some embodiments of the present invention.

FIG. 3 illustrates endoscope 112 in further detail. As shown in FIG. 3, endoscope 112 includes end effector 206d at the distal end, which includes optics for lighting surgical area 210 and for capturing an image, for example a stereo image, from surgical area 210. End effector 206d can be coupled to a wrist 312 that is connected to shaft 310. Wrist 312 allows for movement of end effector 206d in two degrees of freedom and may be controlled with cables or rods 310 that pass through shaft 310. In some embodiments, some axial movement of end effector 206d can also be controlled by cables or rods 310. Optical fiber (not shown) may also pass through shaft 152d and be coupled to the optics in end effector 206d to both provide light and to transmit the image.

Shaft 152d is connected to instrument interface 150d. Instrument interface 150d, as shown in FIG. 1A, can be coupled to arm 108 of patient side cart 100. In some embodiments, interface 150d couples actuation motors in arm 108 with cables and rods 310 in shaft 152d. Instrument interface 150d includes, then, mechanisms that can be driven by an actuation motor that affect wrist 312 and end effector 206d. Arm 108 can be actuated to provide movement of endoscope 112 along the axis of shaft 152d.

In practice, the optics in end effector 206d can include an ability to zoom the image into or out of surgical area 210. Further, instrument interface 150d or instrument arm 106d has the ability to move endoscope 112 laterally along the axis of shaft 152d, thereby providing a zoom function. Whether a zoom feature in end effector 206d or movement of shaft 152d is used to zoom on an image can be controlled by software operating in the surgical system. End effector 206d can also be moved within a spherical surface by manipulating wrist 312. Movement of end effector 206d with wrist 312 can be used to provide different images of surgical area 210.

Figure 4A:
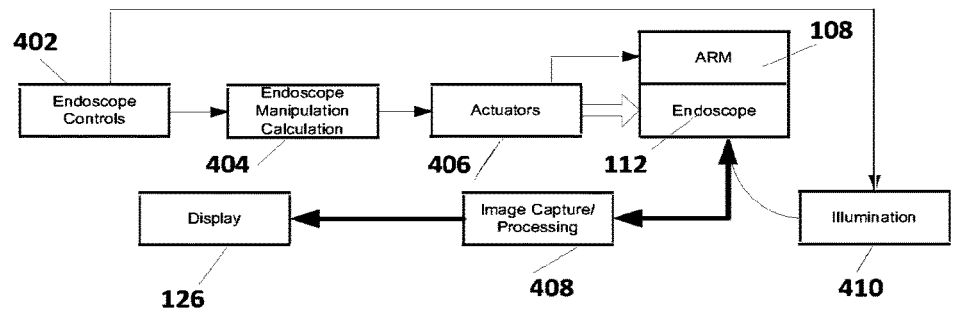
FIG. 4A illustrates an imaging and control system according to some embodiments of the present invention.

FIG. 4A illustrates the control system for an embodiment of endoscope 112 such as that shown in FIG. 3. As shown in FIG. 4A, endoscope controls 402 provide control signals to endoscope manipulation calculation 404. Endoscope controls 402 can be controls according to some embodiments of the present invention, as described below, or may be input signals from MTMs 122 as described above.

Endoscope controls 402 may include processing capability to receive signals from one or more sensors and determine from those signals what the surgeon intends for the change in the image. For example, endoscope controls 402 can determine whether the surgeon requests a zoom function or whether the surgeon requests that the image be panned and in which direction the image should be panned. As such, endoscope controls 402 may include one or more processors coupled with memory (volatile, nonvolatile, or a combination) to hold data and programming instructions. The programming instructions may include instructions to translate signals received from the one or more sensors into signals that represent the requested action of the image produced by endoscope 112.

Endoscope manipulation calculation 404 provides signals to actuators 406. Actuators 406 are mechanically coupled to instrument interface 150d on endoscope 112. Therefore, endoscope manipulation calculation 404 translates the signals received from endoscope controls 402 into actions performed by actuators 406 that result in the corresponding motion of end effector 206d of endoscope 112. As discussed above, the motion of end effector 206d can be axial in end effector 206d (zooming end effector 206d using internal optics or by movement of end effector 206d along its axis), can be lateral by movement of wrist 312 which results in movement of the tip of end effector 206d along a substantially spherical surface, or can result in axial motion of endoscope 112 along the axis of shaft 152d. Zoom and image adjustments can be performed by combinations of various motions that are communicated through instrument interface 150d.

Endoscope manipulation calculation 404 can include a processor executing instructions that calculate the motions that actuators 406 perform in order to result in the motion according to the surgeon input at endoscope controls 402. As discussed above with respect to endoscope controls 402, endoscope manipulation calculation 404 can include one or more processors coupled to memories (volatile, nonvolatile, or a combination) that hold data and programming. In some embodiments, endoscope controls 402 and endoscope manipulation calculation 404 can be performed by the same processors executing the appropriate program instructions.

In some cases, endoscope controls 402 can include MTMs 122. In accordance with some embodiments of the present invention, endoscope controls 402 can include sensors in headrest 130 and can be controlled by the surgeon's motion of his head on headrest 130. Endoscope controls 402 included in headrest 130 are discussed in further detail below. In some embodiments, endoscope controls 402 can include sensors positioned on surgeon's console 120 that track the motion of the surgeon's head.

Endoscope manipulation calculation 404 provides signals to operate actuators 406. Actuators 406 are generally rotary motors housed in patient side cart 100 arm 108, on which endoscope 112 is attached, and drive interface 150d and arm 108. As discussed above, instrument interface 150d translates the mechanical inputs of actuators 406 into movement of wrist 312 and end effector 206d.

Endoscope controls 402 can also control the light output of illumination 410. Illumination 410 provides light through optical fiber in endoscope 112 in order to illuminate surgical area 210 (FIG. 2). An image of surgical area 210 is captured by end effector 206d and transported by optical fiber to image capture and processing 408. Image capture and processing 408 digitizes the image captured by end effector 206d and provides that image to display 126 on surgeon's console 120 (FIG. 1B).

As illustrated in FIG. 4A, the surgeon controls the positioning of end effector 206d through endoscope controls 402. Endoscope controls 402 can include MTMs 122 in an endoscope manipulation mode. In accordance with some embodiments of the present invention, endoscope controls 402 can include input from sensors embedded in headrest 130 or other sensors positioned on surgical console 120.

Figure 4B:
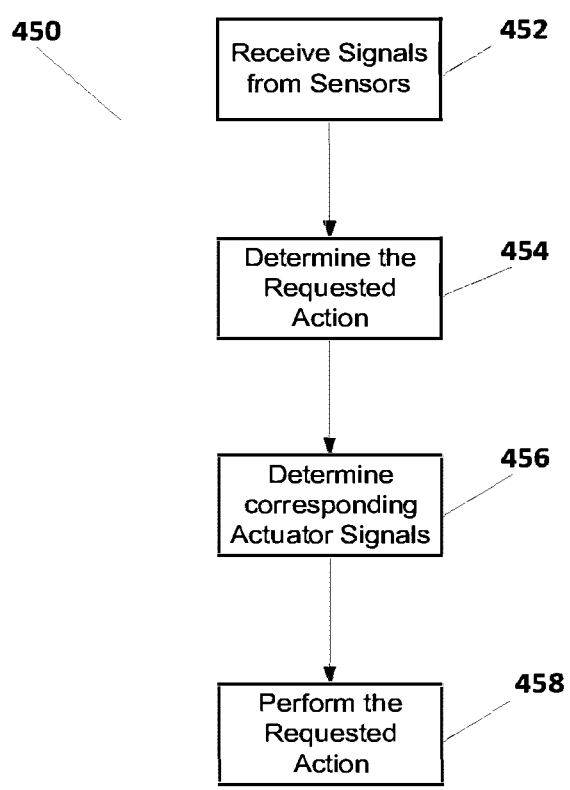
FIG. 4B illustrate a process that can be executed to control an endoscope according to the present invention.

FIG. 4B illustrates a procedure 450 according to some embodiments that can be performed between endoscope controls 402 and endoscope manipulation 404. As shown in FIG. 4B, in step 452 endoscope controls 402 receives signals from one or more sensors mounted on surgeon's console 120. In some embodiments, the sensors are integrated with headrest 130. In some embodiments, the sensors are integrated with surgeon's console 120. The sensors detect a surgeon's input respecting control of endoscope 112. For example, the sensors can provide signals related to the surgeon's head movement or eye movement.

In step 454, the action requested by the surgeon is determined by endoscope controls 402 based on the signals from the one or more sensors. Such actions can include panning the image generated by endoscope 112 or zooming in or out of the image generated by endoscope 112. For example, a detected rotation of the surgeon's face to the right may be interpreted as a request to pan the image to the right while a movement of the surgeon's face into console 120 may be interpreted as a request to zoom into the image.

In step 456, the action requested by the surgeon determined in step 454 is translated to input actuation signals for actuators 406 that drive endoscope 112 and robot arm 108 to perform the requested action. For example, a zoom request may result in signals that drive robot arm 108 or to zoom with the optics in end effector 206d. A pan request results in activation of wrist 312 in the appropriate direction through interface 150d. In step 458, the actuation signals are applied to actuators 406 to perform the requested action.

FIGS. 5A through 5E illustrate an example of a headrest 130 that can be attached to the surgeon console 120. The example of headrest 130 shown in FIGS. 5A through 5E are presented for illustration only and are not meant to be limiting. One skilled in the art will recognize that a headrest can take a variety of shapes, any of which can be used according to some embodiments of the present invention.

Figure 5A:
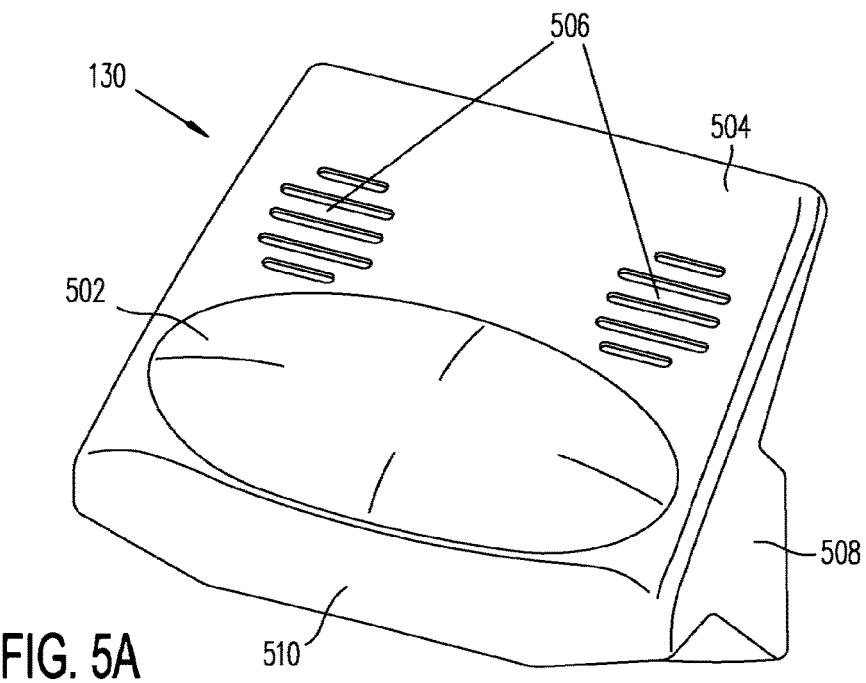
FIGS. 5A, 5B, 5C, 5D, and 5E illustrates a headrest.
Figure 5B:
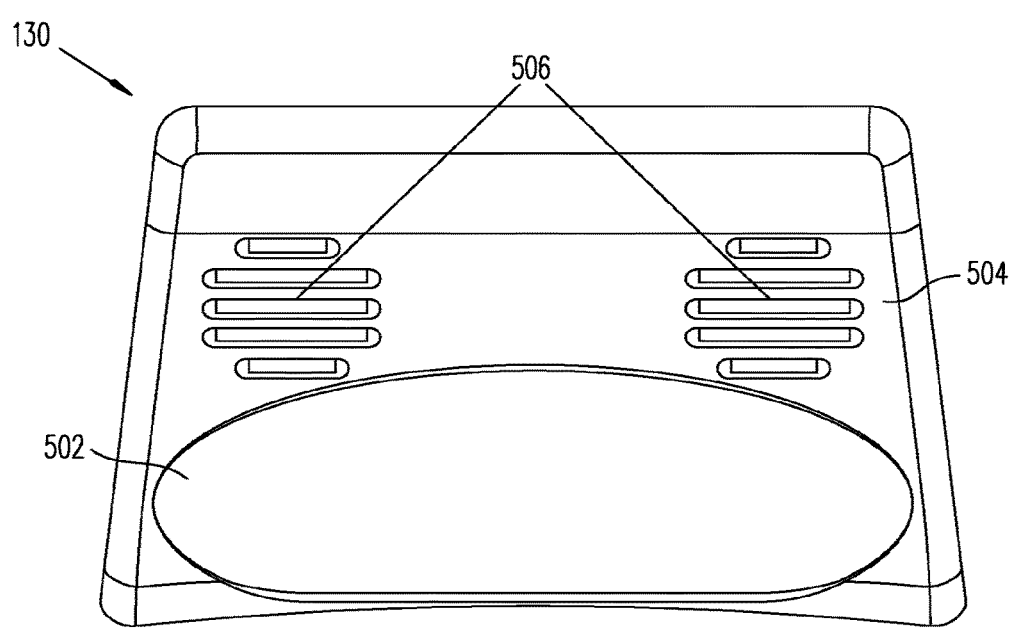

In some cases, headrest 130 can be molded out of foam and covered with, for example a vinyl covering, for both decoration and functionality. FIG. 5A illustrates a generally frontal view of headrest 130. As shown in FIG. 5A, a forehead rest 502 is formed against which a surgeon's forehead can rest while viewing an image of surgical area 210 through display 126. In some cases, speaker grills 506 can be formed in an upper portion 504 above forehead rest 502 to allow sound from speakers mounted behind speaker grills 506 to reach the surgeon. A curved front 510 can be formed below forehead rest 502. A mounting portion 508 can be formed integral with upper portion 504 and forehead rest 502. FIG. 5B illustrate a view of headrest 130 that further shows speaker grills 506 and forehead rest 502.

Figure 5C:
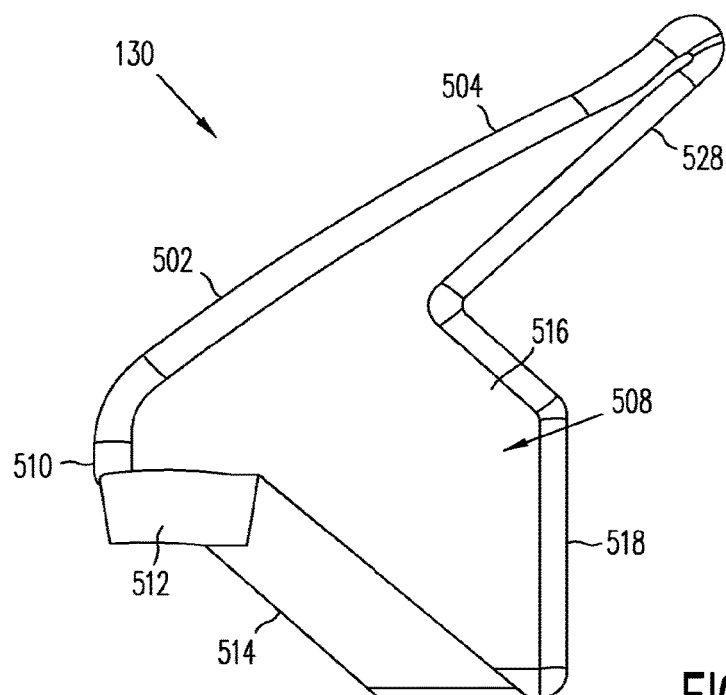

FIG. 5C illustrates a side view of an example headrest 130. As shown in FIG. 5C, mounting portion 508 can be shaped to facilitate mounting on surgeon's console 120. In the example illustrated in FIG. 5C, mounting portion 508 includes side surface 516, back surface 518, upper back surface 528, and bottom surfaces 514 and 512 that serve to position and support headrest 130 against surgeon's console 120.

Figure 5D:
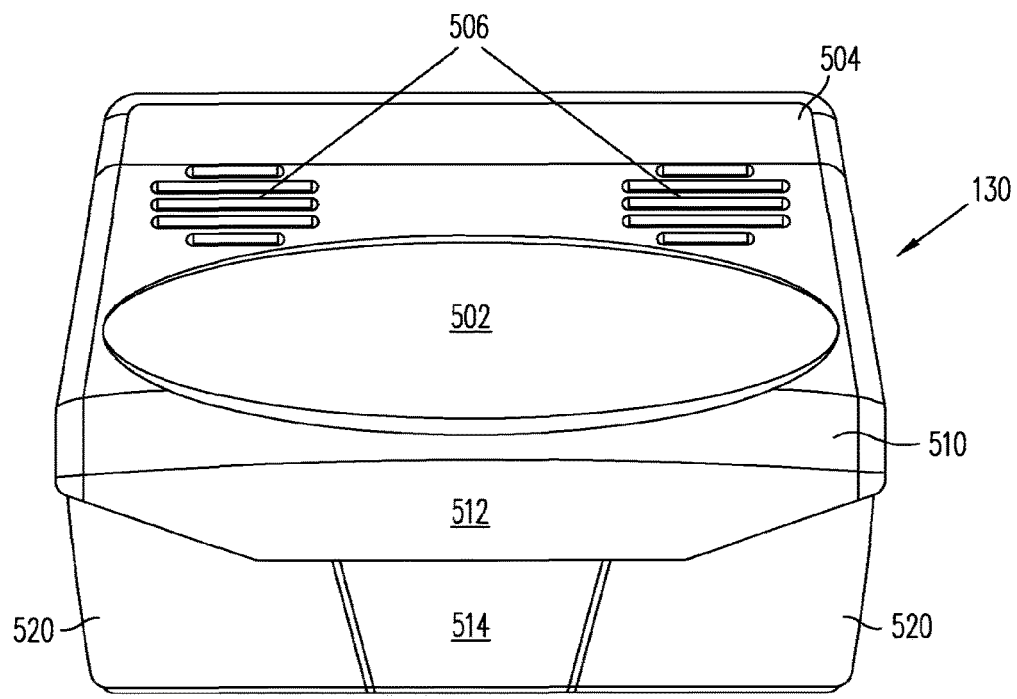
Figure 5E:
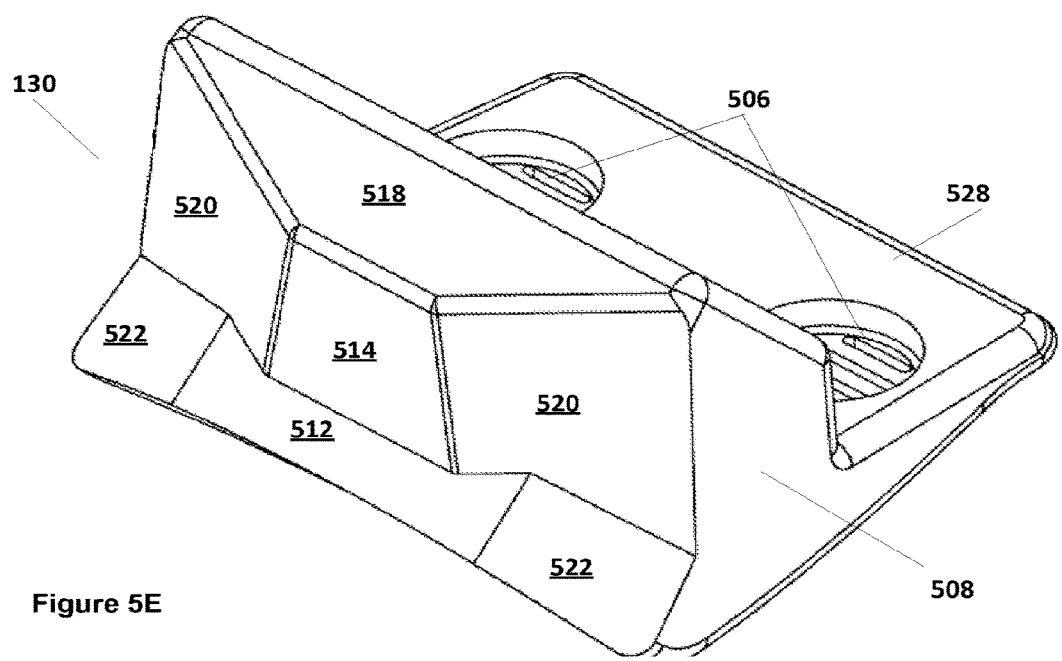

FIGS. 5D and 5E provide further views of headrest 130. FIG. 5D shows generally a frontal view with a showing of rounded surface 512 and bottom surface 514. As shown in FIG. 5D, two angled surfaces 520 can be formed adjacent to bottom surface 514. FIG. 5E illustrates a more detailed bottom view of headrest 130, where surface 512 is adjacent angle surfaces 522.

The shape of mounting portion 508 is dependent on the mounting of headrest 130 onto surgeon's console 120. As such, the shape of mounting portion 508 can be as varied as the number of mounting configurations that can be used for attaching headrest 130 onto surgeon's console 120.

In accordance with some embodiments of the present invention, sensors are embedded within or on headrest 130 to allow the surgeon to provide input signals for endoscope controls 420 by motion of the surgeon's head. In some embodiments, for example, a pressure sensor array can be embedded in headrest 130. The pressure sensor array can sense pressure that the surgeon applies to areas of the front surface of forehead rest 502. The pressure data from the pressure sensor array can then be converted into endoscope control data. In some embodiments, a rocker plate can be inserted into headrest 130. The rocker plate can operate, for example, similarly to a joystick so that endoscope control data can be obtained by the motion of the surgeon's head against the front surface of forehead rest 502. In some embodiments, an optical arrangement can be provided to read the movement of a slip plate mounted on headrest 130. The motion of the slip plate is controlled by the surgeon's head motion and can be converted to control data.

In some further embodiments, a face tracker system can be mounted on headrest 130 or directly on surgeon's console 120. The face tracker can be used to track the motion of the surgeon's face and convert that motion to endoscope control data. In some embodiments, an iris tracker system can be included in display 126 that can be used to track the motion of the surgeon's eyes. Depending on the type of viewer in display 126, the iris tracker sensors can be included in the optics or, if the viewer is a video screen, can be mounted on headrest 130 or on surgeon's console 120 so as to track the motion of the surgeon's eyes and convert that motion to endoscope control data.

Some embodiments of the current invention include endoscope controls 402 attached to or within headrest 130. Endoscope controls 402 include sensing techniques that can control some or all of the position and zoom level (optically or digitally) of an endoscope 112 in a surgical robotic system. In some embodiments, the sensing techniques can capture a sensor signature in two-dimensions to determine the direction of camera movement, and in a third dimension to control the zoom (in/out motion) of the endoscope camera. As such, embodiments of the present invention provide an alternative mode for the surgeon to enter where the endoscope camera is actively controlled simultaneously with the surgical instruments. Many of these systems are further discussed below. In some, a sensor input device is mounted into or onto headrest 130 in order to track the surgeons head motions. The head motion signals are then converted to endoscope control signals in endoscope controls 402 as shown in FIG. 4.

Figure 6A:
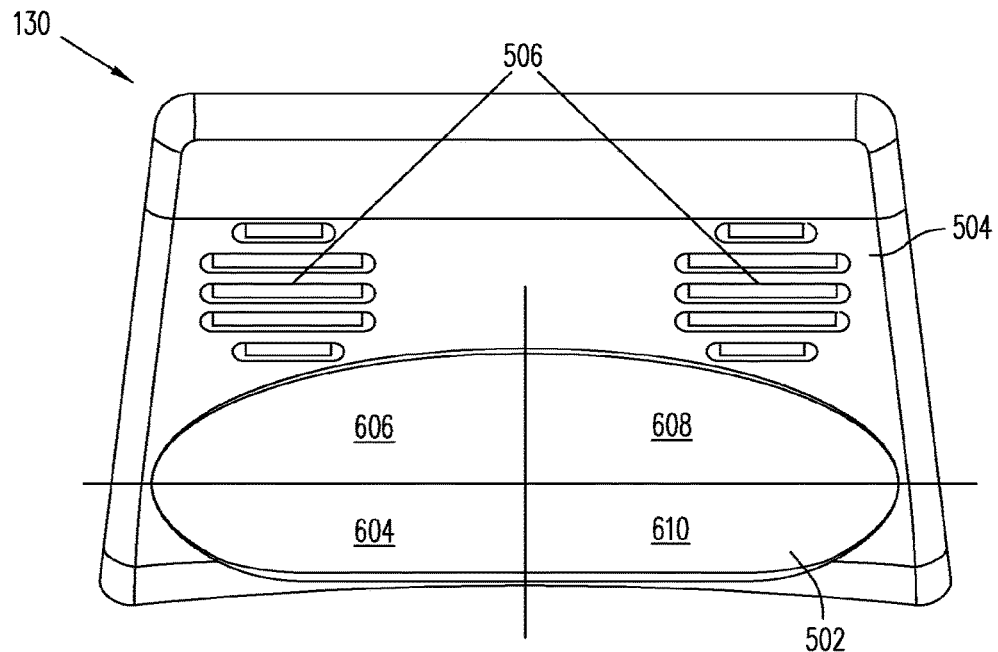
FIGS. 6A, 6B, 6C, 6D, and 6E illustrate an embodiment of the headrest according to the present invention.
Figure 6B:
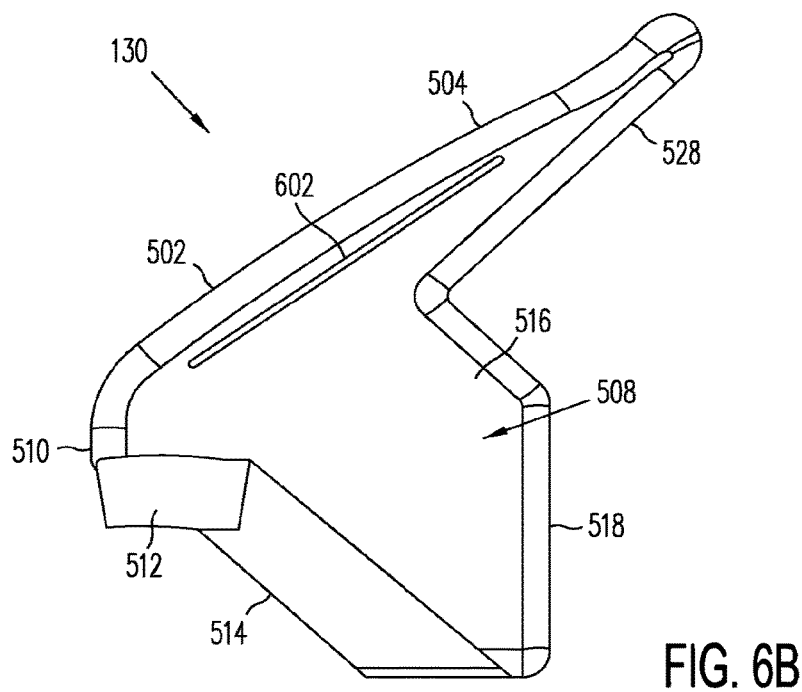
Figure 6C:
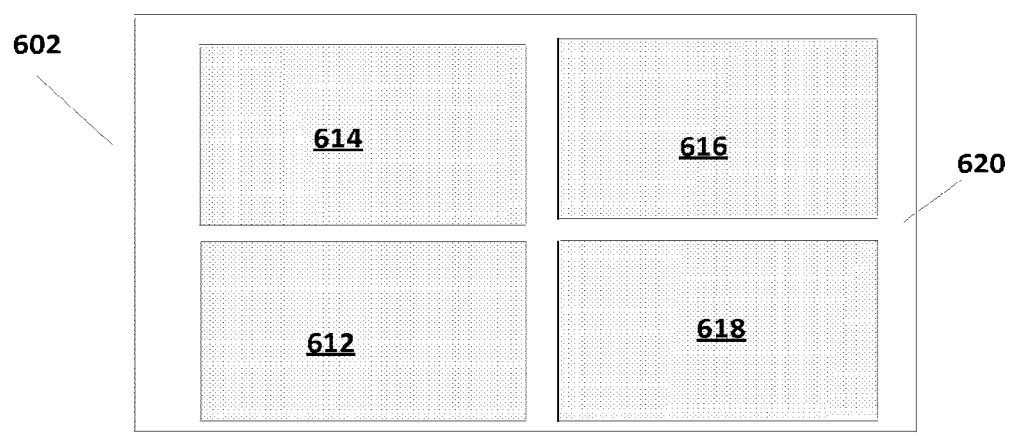

FIGS. 6A, 6B, and 6C illustrate placement of a pressure sensor array 602 in headrest 130. As shown in FIG. 6B, pressure sensor array 602 can be inserted into headrest 130 in close proximity to forehead rest 502 such that the surgeon can provide pressure inputs to areas of the surface of forehead rest 502 by moving the surgeon's forehead. FIG. 6C, for example, illustrates an example of sensor array 602. As shown in FIG. 6C, sensor array 602 can include a two dimensional array of sensors mounted on a planar circuit board or backplane 620. FIG. 6C shows an example with pressure sensors 612, 614, 616, and 618, although pressure sensor array 602 can include any number of pressure sensors mounted on planar backplane 620.

As illustrated in FIG. 6B, pressure sensor array 602 can be positioned substantially parallel with the surface of forehead rest 502. In some embodiments, pressure sensor array 602 can be contoured to follow the shape of forehead rest 502. Further, pressure sensor array 602 can be provided with a support (not shown) that prevents motion relative to surgeon's console 120. Such support can, for example, be studs that extend from pressure sensor array to attach to or contact with sturgeon's console 120.

As shown in FIG. 6A the surface of forehead rest 502 is petitioned into areas according to the placement of individual pressure sensors in pressure sensor array 602 located beneath the surface of forehead rest 502. In the particular example of pressure sensor array 602 with four pressure sensors illustrated in FIG. 6C, the surface of forehead rest 502 is partitioned into four areas where one pressure sensor is placed beneath each of the areas. As illustrated, for example, area 604 corresponds to pressure sensor 612, area 606 corresponds to pressure sensor 614, area 608 corresponds to pressure sensor 616, and area 610 corresponds to pressure sensor 618. In other words, pressures sensor 612 senses the pressure applied to area 604, pressure sensor 614 senses the pressure applied to area 606, pressure sensor 616 senses the pressure applied to area 608, and pressures sensor 618 senses the pressure applied to area 610. Pressure applied to areas 604 through 610 and sensed by pressure sensors 612 through 618, respectively, can be used to provide signals for endoscope controls 402.

Pressure sensing array 602 is integrated into headrest 130, which is mounted on surgeon's console 120, within the foam under forehead rest 502, where the surgeon rests his/her forehead. Surgeon's console can then be electrically coupled to pressure sensing array 602 to record the pressure signature of the surgeon's forehead against forehead rest 502. As shown in FIG. 6A, this signature can be divided into multiple regions (areas 604 through 610 are illustrated in FIG. 6A) to determine the direction of camera motion indicated by the surgeon's motion.

Figure 6D:
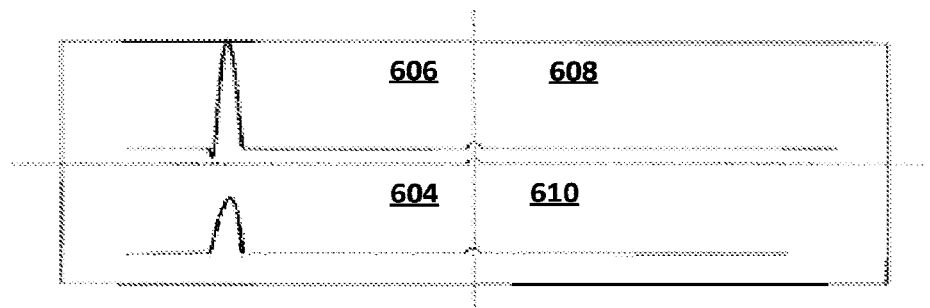

For example, to move end effector 206d of end effector 112 such that the image viewed at display 126 is moved to the right, the surgeon can, for example, roll their head slightly to the left to create a pressure profile with larger magnitudes in the left hand side of the array. The pressure profile for this example is illustrated in FIG. 6D. As shown in FIG. 6D, pressure sensors 612 and 614 measure increased pressure in areas 604 and 606. In response to the data shown in FIG. 6D, end effector 112 can be manipulated to move the image to the right. Alternatively, a surgeon's head roll to the left in some embodiments may result in movement of the image to the left.

In some embodiments, the velocity of the image movement can be a constant, which may be set by a surgeon input elsewhere on surgeon's console 120. In some embodiments, the velocity of the image movement can vary based on the magnitude of the forces within the signature as shown in FIG. 6D. In some embodiments, the speed of motion of the image can be audibly indicated to the surgeon. For example, the speed of motion of the image can be indicated with audible clicks whose frequency indicates the speed of motion. In some embodiments, for example, the speed of motion can be indicated by volume or frequency of a tone.

In addition to audible feedback, visual feedback and haptic feedback, or other feedback mechanisms can be used to communicate information to the surgeon. Visual feedback, for example, can be provided to the surgeon through display system 126 and may, for example, be a flashing light with frequency indicating the speed of motion or may be color coded so that different colors indicate different speeds. Additionally, haptic feedback may be included in headrest 130. For example, through haptic feedback in headrest 130 a vibration, the frequency of which indicates the speed, is transmitted to the surgeon.

Figure 6E:
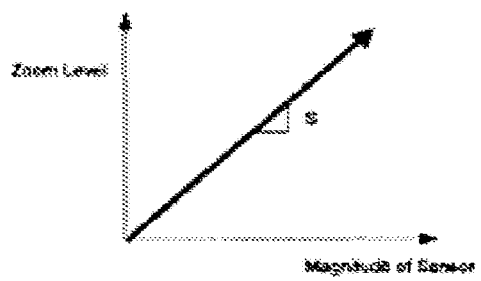

In some embodiments, a pressure profile indicating force perpendicular to the surgeon's forehead can indicate a request in/out motion of the endoscope 112 (motion along the endoscope shaft 152d), or to control the level of zoom. For example, as illustrated in FIG. 6E a linear relationship between the magnitude of the force perpendicular to the forehead rest 502 and the zoom level can be established. In that example, when the surgeon is operating in this control mode the surgeon can affect a zoom by pressing their forehead a little harder against the forehead rest 502 to zoom in and let up on the pressure to zoom out. The slope of this relationship, controlling the rate of zoom adjustment, can be a parameter that the user sets via the surgeon console touchpad or vision cart touch panel interface.

Figure 7:
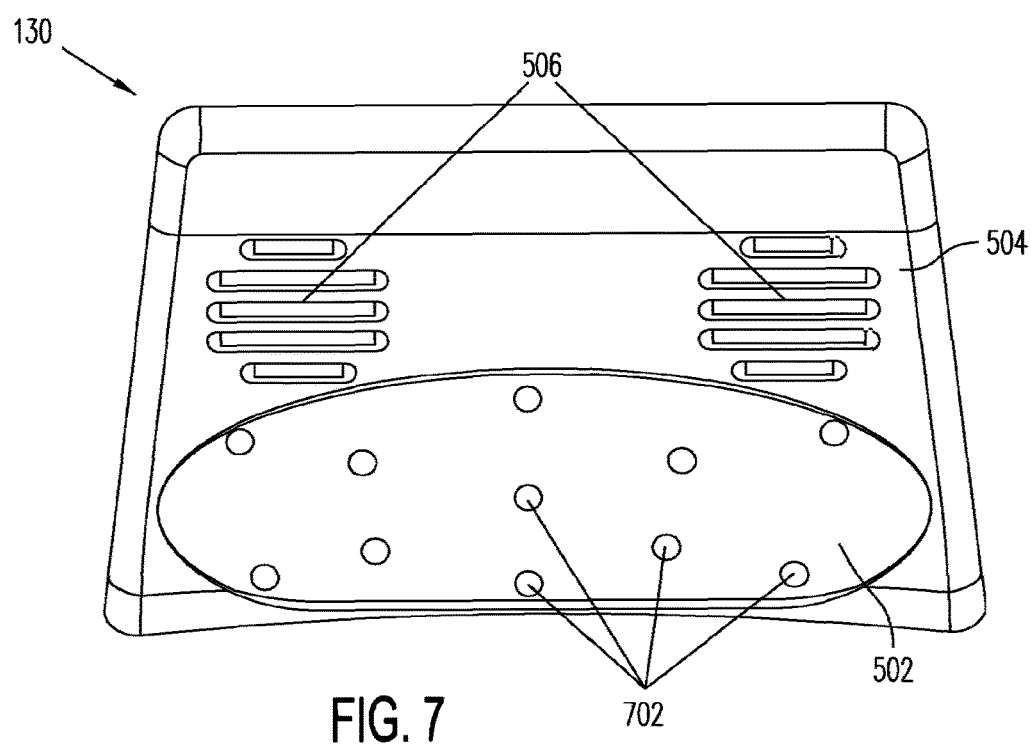
FIG. 7 illustrates another embodiment of the headrest according to the present invention.

In some embodiments, surgeon headrest 130 can include detectors, for example proximity detectors, that determine the location of the surgeon's head from a fixed point. The fixed point can, for example, represent the tip of the endoscope camera (i.e. the tip of end effector 206d). Movement in the surgeon's head can then control endoscope motion, including image location and zoom. FIG. 7 illustrates an embodiment of headrest 130 that includes one or more sensors 702 embedded under the surface of forehead rest 502 that collectively can determine the position and orientation of the surgeon's forehead relative to the fixed point.

As discussed above, sensors 702 can be coupled to provide signals for analysis in endoscope controls 402. Endoscope controls 402 then can determine the location and/or the orientation of the surgeon's forehead. There may be any number of sensors 702. Sensors 702 can, for example, be proximity sensors that measure the distance to the surgeon's forehead. For example, a single centered proximity sensor can be used as a zoom control, moving the camera in and out as the surgeon's forehead moves closer and further from forehead rest 502. Other sensors can be used to determine side-to-side or up-and-down motions of the surgeon's forehead. Therefore, as the surgeon's head moves, the distance from the fixed point defined by the collection of sensors 702 is measured, and used as an input to control the camera. The perpendicular distance from the fixed point could be used to create a relationship between the zoom level and the distance from the fixed point to actively control the zoom. For example, as the surgeon's head rolls to the left, sensors 702 on the left of forehead rest 502 may measure closer distances and sensors 702 on the right of forehead rest 502 may measure farther distances. This data can be used in endoscope controls 402 to indicate that the surgeon has rolled his head to the left and endoscope 112 can be controlled accordingly.

Figure 8:
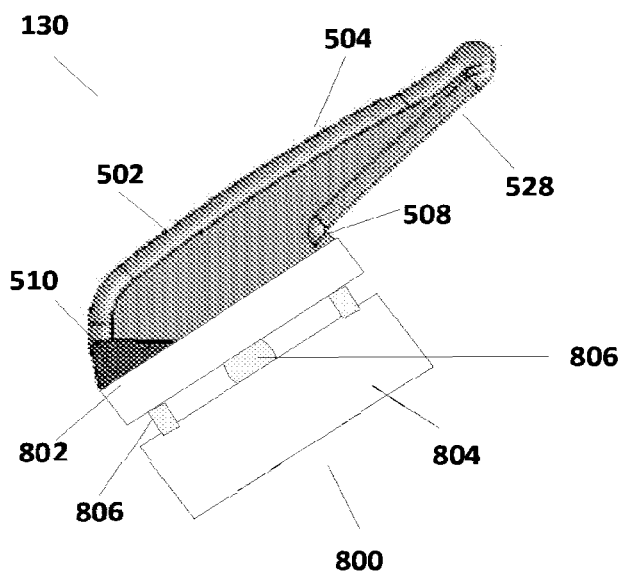
FIG. 8 illustrates another embodiment of the headrest according to the present invention.

FIG. 8 illustrates an embodiment where headrest 130 is mounted to a controller 800 that can be similar to a joystick. In the example of joystick controller 800 shown in FIG. 8, controller 800 can include a first plate 802 that is fixed to headrest 103, for example opposite forehead rest 502. First plate 802 can include a ball 806 fixed to first plate 802. A sensor plate 804 can include a recess to receive ball 806 and sensors that determine the rotational orientation of ball 806 within the recess of sensor plate 804. In some embodiments, ball 806 can be replaced with a rod that is coupled to a receiver in sensor plate 804. As is further shown, springs 806 can be inserted between first plate 802 and sensor plate 804 to provide tension that biases headrest 103 toward a neutral position. In some embodiments, sensor plate 804 can detect additional pressure along a normal direction to sensor plate 804. Two-dimensional motion of the camera can therefore be controlled by rolling first plate 802 in a particular direction to cause endoscope 112 to move the image in a corresponding direction. Pressure along the normal direction can be used to activate motion of the camera through headrest 130 or can be used to control zoom of the camera of endoscope 112.

Figure 9:
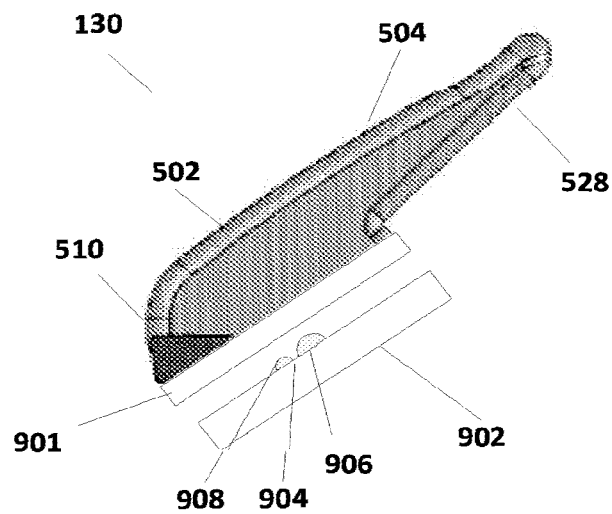
FIG. 9 illustrates another embodiment of the headrest according to the present invention.

FIG. 9 illustrates another embodiment of headrest 130. As shown in FIG. 9, headrest 130 can be connected to a slip plate 901, which is allowed to slide in two dimensions with respect to surgeon's console 120. A detector plate 902 can be fixed on surgeon's console 120 so that slip plate 901 moves with respect to detector plate 902. Detector plate 902 can include, for example, an optical detector similar to an optical mouse that monitors movement of slip plate 901. Movement of the surgeon's head then causes slip plate 901 to move relative to detector plate 902, resulting in a signal that can be used in endoscope controls 402 to control endoscope 112. For example, optical tracker 904, which may include an optical source 906 and optical detector 908 pair, provides a signal that indicates the motion of slip plate 901 relative to detector plate 902. Motion of slip plate 901 indicating left or right motion of the surgeon's head can provide signals in endoscope controls 402 to move the image from endoscope 112 left or right and motion of the surgeon's head up or down can provide signals to endoscope controls 402 to move the image from endoscope 112 up or down.

Figure 10:
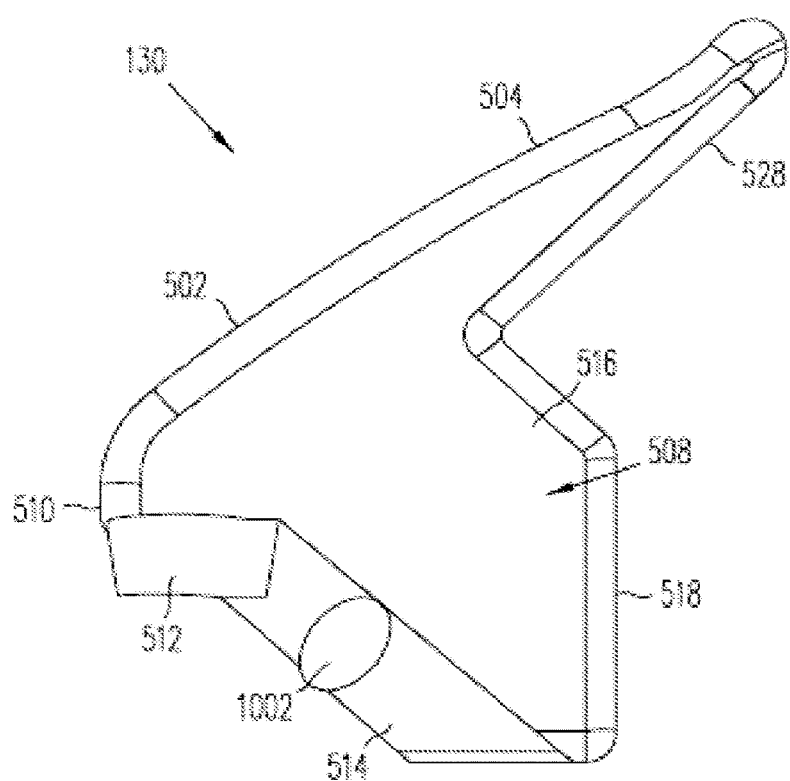
FIG. 10 illustrates another embodiment of the headrest according to the present invention.

In some embodiments, face tracking can be used to track the surgeon's facial orientation and determine when and how the surgeon's face moves. FIG. 10 illustrates a headrest 130 according to some embodiments of the present invention that includes a camera 1002 that can be used in face tracking software. Camera 1002 can provide images to endoscope controls 402, which can analyze the images to perform face tracking. Therefore, endoscope controls 402 perform face tracking to determine the orientation of the surgeon's face relative to the surgeon's console 120. Movement of the face can then be used to control movement of endoscope 112. Zoom, for example, can be controlled by the movement of the surgeon's face perpendicular to camera 1002 (or in a direction away from headrest 130) while rotation of the surgeon's face in the plane headrest 130 can be used to control the planar motion of endoscope 112.

Figure 11:
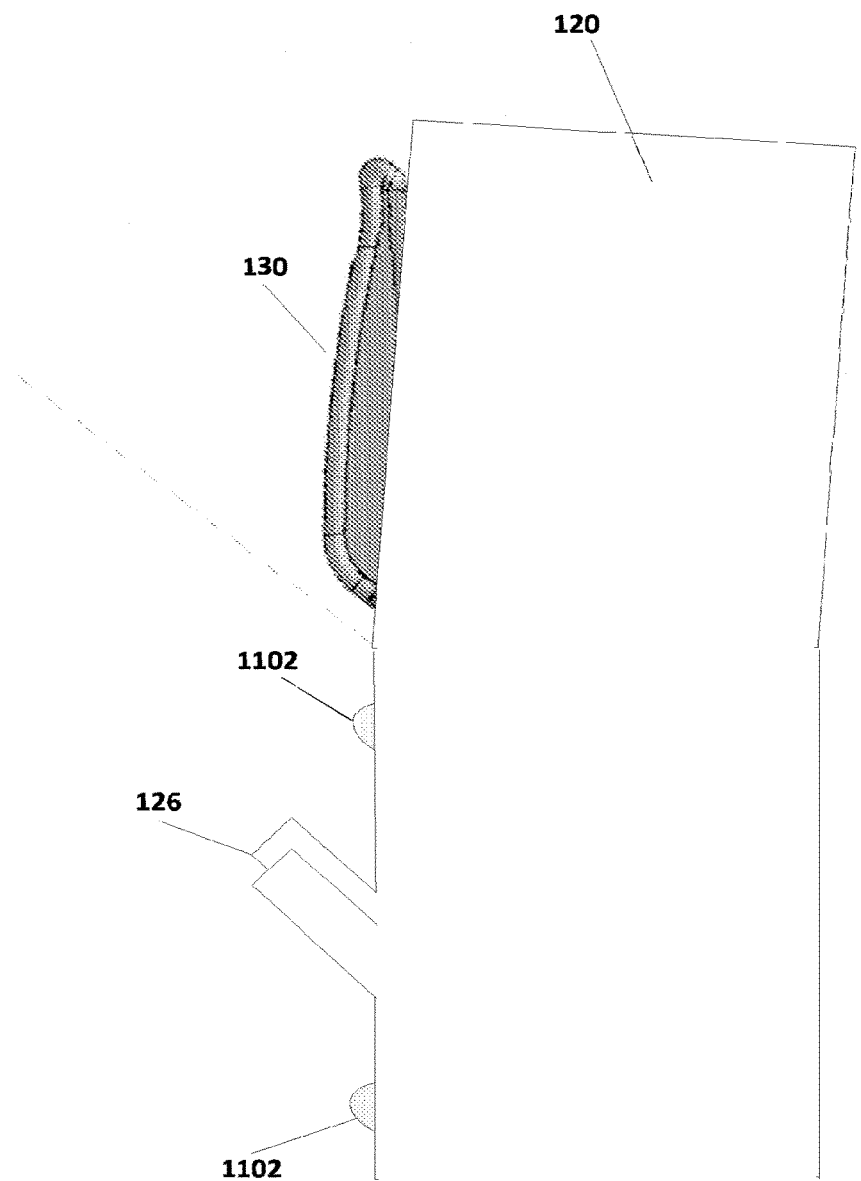
FIG. 11 illustrates an embodiment of the invention.
Figure 12:
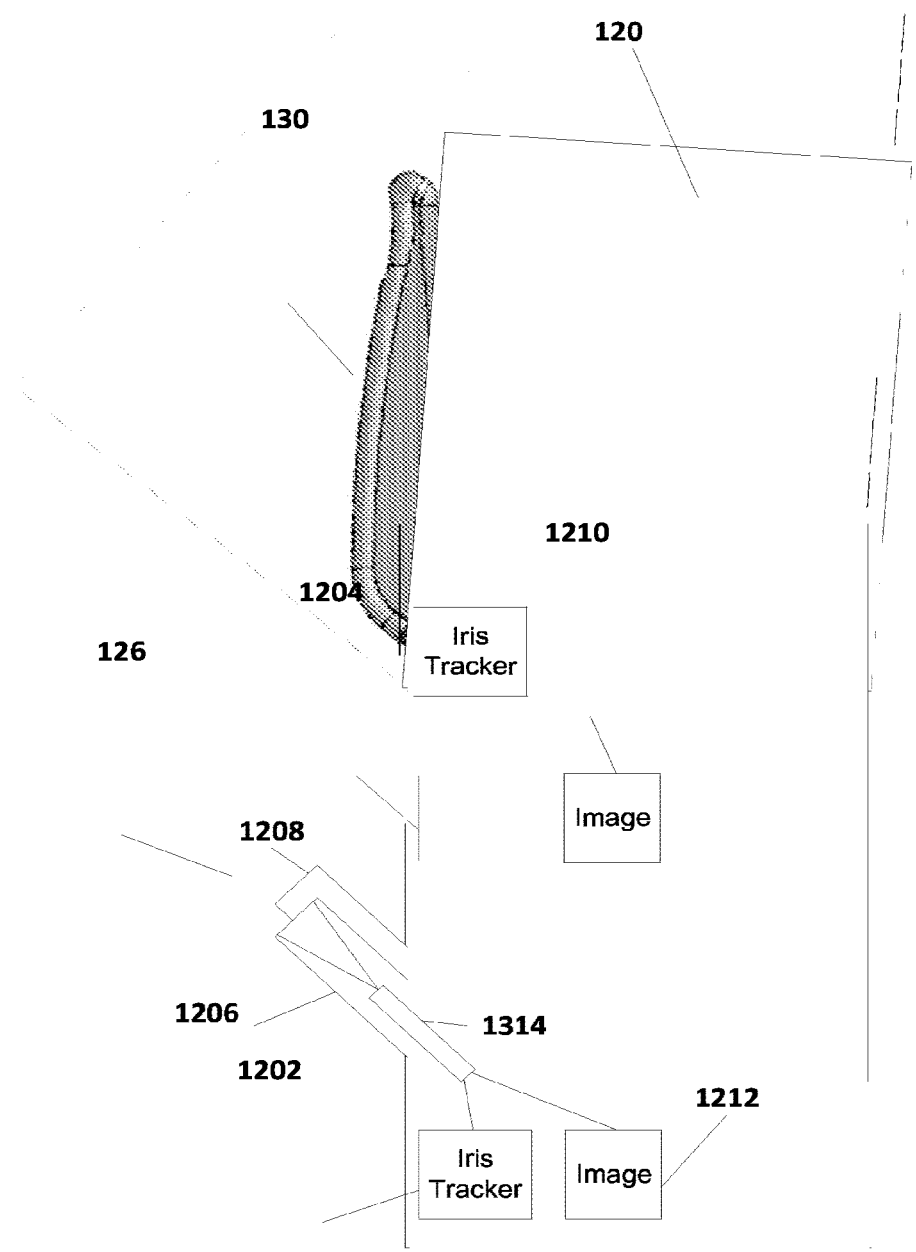
FIG. 12 illustrates another embodiment of the invention.

FIG. 11 illustrates another embodiment that uses face tracking to track the surgeon's facial orientation and determine when and how the surgeon's face moves. As shown in FIG. 12, at least one camera 1102 is mounted on surgeon's console below headrest 130 and in proximity to image display 126. Camera 1102 can then provide an image of the surgeon's face that can be analyzed in endoscope controls 402 as described above.

In some embodiments, an iris tracking system can be utilized. FIG. 12 illustrates iris tracking in surgeon's console 120. As shown in FIG. 12, iris tracking 1202 provides an optical tracking beam, which may be an IR beam, that is optically combined in combiner 1214 with image 1212. The combined image is then incident on the surgeon's eye through the right eyepiece 1206. A similar optical arrangement can combine optical tracking beam from iris tracker 1204 with image 1210 which is incident on the surgeon's eye through the left eyepiece 1308. Iris trackers 1202 and 1204 can receive the reflected tracking beam. Signals from iris trackers 1204 and 1202, which are related to movement of the surgeon's eyes, can then be provided to endoscope controls 402. The surgeon can then request an image pan by moving the surgeon's eyes to the area to be centered in the image.

To address the safety concern of accidently moving the camera such that the instruments are outside the field of view the implementation could constrain the camera motion to a predefined region. The control strategy could also integrate tool tracking techniques to allow arbitrary camera motion as long as the instrument tips stay with the field of view. Tool tracking could also be used to ensure that the camera does not collide with the surgical instruments during motion.

In some embodiments, a clutching mechanism may also be included. For example, embodiments of the present invention may be activated with a foot pedal or by a particular motion of the head. Further, to avoid unintended movement, in some embodiments only particularly large motions may result in active control of endoscope 112.

The above detailed description is provided to illustrate specific embodiments of the present invention and is not intended to be limiting. Numerous variations and modifications within the scope of the present invention are possible. The present invention is set forth in the following claims.

What is claimed is:

1. A surgeon's console, comprising:
    an image display system that displays an image of a surgical area; and
    one or more sensors mounted in the surgeon's console to provide a signal related to a movement of a surgeon's face, the image being moved according to the signal;
    wherein the one or more sensors includes at least one of:
        an array of pressure sensors positioned adjacent to a forehead rest surface, each of the pressure sensors corresponding to an area of the forehead rest surface, pressure applied by the surgeon to one or more areas of the forehead rest surface providing input to the pressure sensor array to generate the signals;
        a joystick control mounted in a headrest, the joystick controller comprising a first plate attached to the headrest, a sensor plate, and a controller coupled between the first plate and the sensor plate so that motion of the headrest is detected; or
        a slip plate mounted to the headrest, the slip plate communicating with an optical detector positioned to detect motion of the slip plate, wherein the slip plate positioned to move with the surgeon's head.

2. The surgeon's console of claim 1, wherein a speed that the image is moved is indicated on the surgeon's console.

3. The surgeon's console of claim 2, wherein the speed is indicated by one or more of:
    a frequency of audible clicks;
    a frequency of a flashing light; or
    a color coded indicator.

4. A headrest for a surgical console, comprising:
    a forehead rest surface;
    a headrest mount configured to attach to the surgical console; and
    one or more sensors in the headrest that detect inputs from a surgeon's head and provide signals based on the inputs to an endoscope control;
    wherein the one or more sensors include pressure sensors arranged as a pressure sensor array positioned adjacent to the forehead rest surface, each of the pressure sensors corresponding to an area of the forehead rest surface, pressure applied by the surgeon to one or more areas of the forehead rest surface providing input to the pressure sensor array to generate the signals.

5. The headrest of claim 4, wherein the endoscope control determines an endoscope action based on the signals.

6. The headrest of claim 5, wherein the endoscope control is configured to cause a zoom of an image provided by an endoscope in response to pressure at a center of the forehead rest surface and to cause a pan of the image provided by the endoscope in response to pressure at an area of the forehead rest surface other than the center.

7. The headrest of claim 4, wherein a speed at which an image captured by an endoscope controlled by the endoscope control is moving is indicated.

8. The headrest of claim 7, wherein the speed is indicated by a frequency of audible clicks.

9. The headrest of claim 7, wherein the speed is indicated by a frequency of a flashing light.

10. The headrest of claim 7, wherein the speed is indicated by a color coded indicator.

11. A headrest for a surgical console, comprising:
a forehead rest surface;
a headrest mount configured to attach to the surgical console; and
one or more sensors in the headrest that detect inputs from a surgeon's head and provide signals based on the inputs to an endoscope control;
wherein the headrest is coupled to a joystick controller, the joystick controller comprising:
a first plate attached to the headrest;
a sensor plate; and
a controller coupled between the first plate and the sensor plate so that motion of the headrest is detected.

12. The headrest of claim 11, wherein a speed at which an image captured by an endoscope controlled by the endoscope control is moving is indicated.

13. The headrest of claim 12, wherein the speed is indicated by a frequency of audible clicks.

14. The headrest of claim 12, wherein the speed is indicated by a frequency of a flashing light.

15. The headrest of claim 12, wherein the speed is indicated by a color coded indicator.

16. A headrest for a surgical console, comprising:
a forehead rest surface;
a headrest mount configured to attach to the surgical console; and
one or more sensors in the headrest that detect inputs from a surgeon's head and provide signals based on the inputs to an endoscope control;
wherein the one or more sensors includes a slip plate mounted to the headrest, the slip plate communicating with an optical detector positioned to detect motion of the slip plate, wherein the slip plate positioned to move with the surgeon's head.

17. The headrest of claim 16, wherein a speed at which an image captured by an endoscope controlled by the endoscope control is moving is indicated.

18. The headrest of claim 17, wherein the speed is indicated by a frequency of audible clicks.

19. The headrest of claim 17, wherein the speed is indicated by a frequency of a flashing light.

20. The headrest of claim 17, wherein the speed is indicated by a color coded indicator.

* * * * *